United States Patent [19]

Anzenberger, Sr.

[11] 4,402,883

[45] Sep. 6, 1983

[54] RECLAMATION OF ORGANOPHOSPHATE FLUIDS

[75] Inventor: Joseph F. Anzenberger, Sr., New City, N.Y.

[73] Assignee: Stauffer Chemical Co., Westport, Conn.

[21] Appl. No.: 309,652

[22] Filed: Oct. 8, 1981

[51] Int. Cl.³ ............................................... C07F 9/09
[52] U.S. Cl. .................................. 260/990; 423/658.5
[58] Field of Search ...................... 260/990; 423/658.5

[56] References Cited

U.S. PATENT DOCUMENTS 4,227,972 10/1980 Hernandez et al. ................. 260/990

Primary Examiner—J. E. Evans
Attorney, Agent, or Firm—Roger S. Benjamin

[57] ABSTRACT

Acidity of used organophosphate containing functional fluids is reduced by contact with activated alumina. The activated alumina is regenerated for reuse by a sequential leaching/heating process.

8 Claims, 1 Drawing Figure

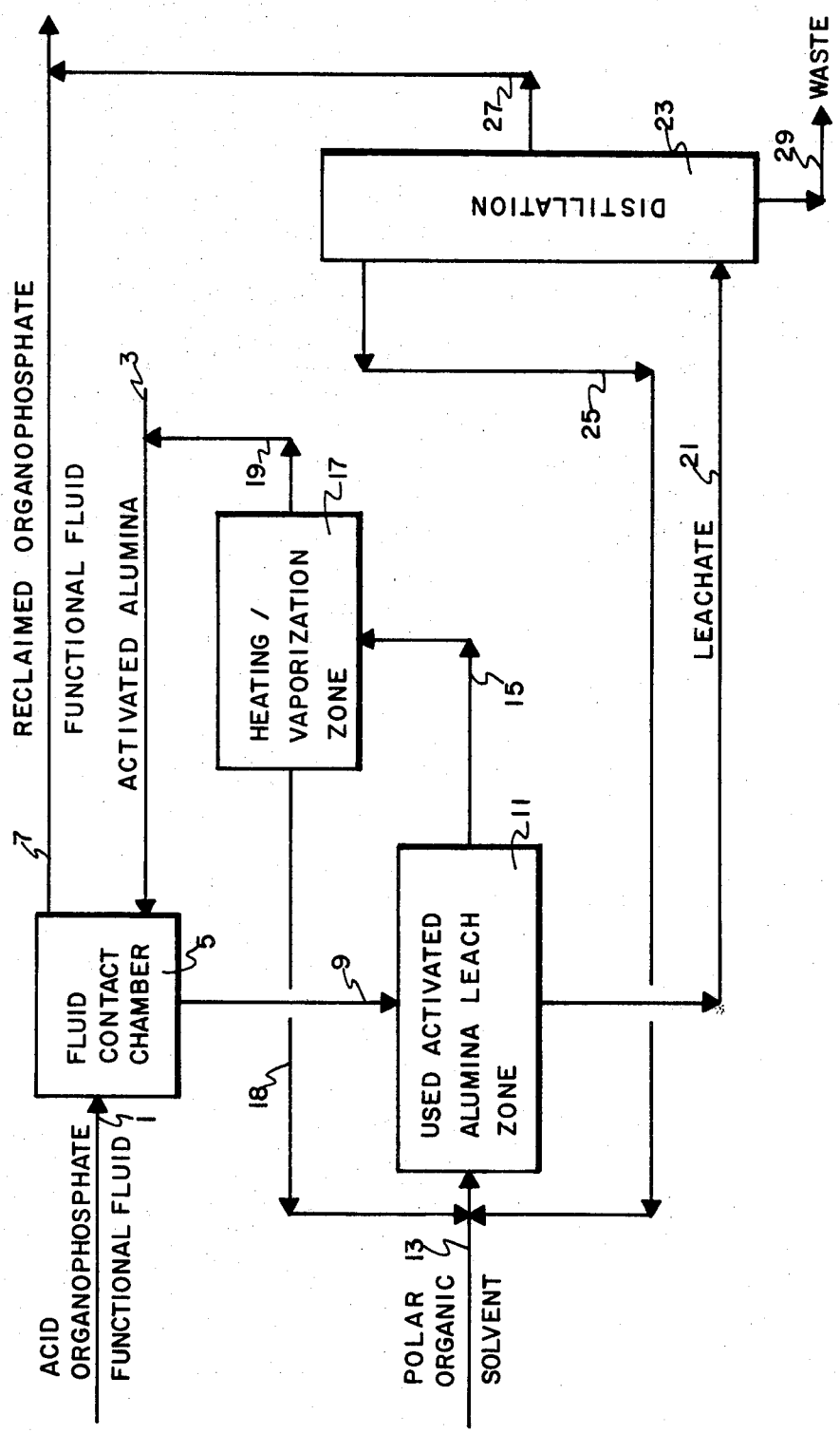

RECLAMATION OF ORGANOPHOSPHATE FLUIDS

BACKGROUND OF THE INVENTION

Phosphate ester based lubricants and hydraulic fluids have long service life and excellent stability. Such fluids are typically based on triaryl phosphates. It is known that from use over a period of time phosphate ester fluids experience degradation which is manifested as increased acidity. This acidity may eventually build to corrosive levels.

A wide variety of methods ar used to deal with the problem of acid buildup in phosphate ester fluids. Acid acceptors such as epoxides may be added to phosphate ester fluids. However, acid neutralization agent by-products may accumulate and may lead to other problems.

Another treatment for overly acidic phosphate ester fluids is contact with neutralizing clays such as Fuller's Earth. A disadvantage of Fuller's Earth treatment is that alkaline earth ions are transferred from the clay into the neutralized ester fluid.

Phosphate ester fluids may also be refined by distillation at reduced pressure. Distillation is effective in purifying organophosphates but this technique demands special equipment and careful process controls. It is desirable to develop improved methods of treating phosphate ester fluids which maintain low acidity without difficult methodolgy or expense.

FIELD OF THE INVENTION

This invention relates to the purification of organophosphate functional fluids.

THE INVENTION

This invention is a process for reducing the acidity of used organophosphate functional fluids by contact with an activated alumina acid-reducing agent.

This invention is also a method of reducing the acidity of organophosphate by contact with acid activated alumina acid-reducing agent and thereafter regenerating the acid-reducing agent.

Moreover, this invention is a method of reducing the acidity of organophosphates, regenerating the acid-reducing agent, and recovering organophosphate retained by the acid-reducing agent.

DETAILED DESCRIPTION OF THE INVENTION

Organophosphate containing functional fluids treated by the process of this invention are the normal esters of phosphoric acid in which all three hydrogens have been substituted by hydrocarbon groups. Suitable organophosphates utilized by this invention are those represented by the formula:

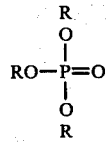

wherein the R groups are the same or different and are selected from alkyl, aryl, aralkyl, or alkaryl radicals having from one to twenty carbon atoms.

Triaryl phosphate functional fluids are preferred for the practice of the invention. Typical triaryl phosphates and methods of synthesis are described in British Pat. No. 837,679; U.S. Pat. No. Re. 29,540; and U.S. Pat. No. 4,139,487, the disclosures of which are incorporated herein by reference. Particularly preferred triaryl phosphates include tricresyl phosphate, cresylphenylphosphates, xylyl phosphates, xylyl/phenylphosphates, isopropylphenyl/phenyl phosphates, secondarybutylphenyl/phenyl phosphates, tertiarybutylphenyl/phenyl phosphates; and mixtures of these phosphates. Teritiarybutylphenyl/phenyl phosphate mixtures containing ditertiarybutylphenyl monophenyl phosphate and monotertiarybutylphenyl diphenyl phosphate have been found to be particularly preferred for the practice of this invention.

The organophosphate functional fluids treated by the process of this invention contain organophosphate as their major component. Optional ingredients in the functional fluid may include, for example, other additives conventional to functional fluids used as plasticizers, lubricants, hydraulic fluids, and etc.

"Activated alumina" constituting the acid-reducing agent of this invention is defined as alumina having a high surface area (over about 200 sq.m./g). Properties and types of activated aluminas suitable for use in this invention are those described as Type 1, Type 2, Type 3, and Type 4, in the *Encyclopedia of Chemical Technology (Kirk-Othmer) Third Edition* Volume 2, pages 225 to 233, published by John Wiley and Sons, (ISBN 0-471-02038-0), the disclosure of which is incorporated herein by reference.

The polar organic solvent used for regenerating the activated alumina employed in the process of this invention is selected from ketones, alcohols, or mixtures thereof having less than seven carbon atoms. Exemplary polar organic solvents having utility in this invention are methanol, ethanol, isopropanol, butanol, acetone, methyl ethyl ketone, or mixtures thereof. Acetone, methanol, ethanol and isopropanol are particularly preferred as solvents.

"Acidity" of an organophosphate or organophosphate functional fluid is defined in the context of this invention as mg. KOH/g of fluid as measured by ASTM D 974 (Neutralization Number by Color Indicator Titration). The acidity level of the organophosphate functional fluid need not be immediately harmful to its surroundings to be considered unacceptable. Unacceptable acidity levels may be only such levels as are indicative of amendatory future action. A generally desirable acidity is in the range of from about 0.03 to about 0.10 mg. KOH/g with an acidity of less than 0.10 being particularly desirable. This invention is not bound by any theory of acid formation but it is believed that acidity of organophosphate fluids is usually due to free arylacid phosphates such as diphenyl acid phosphate, which form in a working environment.

The acidity of organophosphate functional fluids is reduced by contact with activated alumina. The contacting of the fluid and the alumina may be performed in any conventional manner. For example, the alumina may be dispersed in the functional fluid, or the fluid may be moved through a stationary bed of alumina. The amount of alumina required for removal of acid from the fluid is an amount effective to reduce the acid number to an acceptable level. The determination of an effective amount may be determined by taking an aliquot sample of fulid and determining its acidity after treatment with a measured amount of activated alumina by a standard test such as the ASTM D 974. Typically, the organophosphate functional fluid is contacted with at least about one percent activated alumina based on the weight of oganophosphate. Preferably the organophosphate fluid is treated with about one to about five percent activated alumina.

The temperature at which contact of the used organophosphate functional fluid and activated alumina takes place may vary within wide limits, for example, from 0° C. to the boiling point of the fluid. A preferred practice of the invention is to contact the alumina and fluid at above-ambient temperatures; typically, from about 48° C. to about 93° C. These above ambient temperatures promote easy handling of the fluid by reducing viscosity.

The time required for removal of acidity by contact of the organophosphate functional fluid and alumina is not critical, and effective contact times may be determined by testing aliquot samples of fluid undergoing treatment with alumina. Typical treatment times vary from one-half hour to twelve hours.

When the acidity of the organophosphate functional fluid is reduced to an acceptable level, the fluid is separated from the solid alumina by suitable means such as decantation or filtration. It is preferred to remove as much physically separable fluid as practical from the alumina. The resultant "used" alumina containing (acidic) deposits and some entrained organophosphate fluid is next treated to regenerate its acid-reducing properties.

The method of regenerating used activated alumina according to this invention is a two step method having the essential operations of (1) leaching, and (2) heating.

"Leaching" refers to the process operation of extracting acid-causing materials from solid activated alumina by contact with a liquid polar organic solvent.

The volume ratio of activated alumina to polar organic solvent leachate is not critical and may vary over wide limits. Typically, for a batch process the volume ratio of solids to leachate varies from 1:1 to 1:500. The leaching operation is advantageously performed in stages.

The time and temperature of the leaching process is not critical. Leaching periods from about one-half hour to about ten hours are typical. Leaching temperatures near ambient temperature are preferred for cost and convenience although temperatures above the freezing point up to the boiling point of the polar organic solvent may be employed if desired.

Polar organic solvent leaching of the activated alumina has the effect of removing from the activated alumina sorbed acid-causing impurities as well as entrained organophosphate functional fluid. The leaching step may be conducted in any apparatus convenient for such purpose. Suitable apparatus would typically be equipped with means for introduction and removal of both the activated alumina and the polar organic solvent.

The second heating step of the regeneration process has as its object removal of sorbed or entrained polar organic solvent from the leached activated alumina. The general method of solvent removal is heating the alumina while providing means for the removal of vaporized solvent. Vaporization and escape of solvent vapor may be promoted by a moving stream of air, gas, or steam or by use of subatmospheric pressure.

The activated alumina may be heated in the second step of the regeneration process to temperatures up to about 600° C. if desired.

However, it is a particular advantage of this invention that the heating step of the regeneration treatment may be conducted at temperatures of less than 160° C. In particular, using solvents selected from the group methanol, ethanol, acetone, methyl ethyl ketone temperatures of less than 100° C., typically from 50° to 99° C. are employed.

The heating step is conducted until at least the weight of solvent and sorbed acidic components retained by the alumina is less than twenty weight percent of the original dry weight of activated alumina (measured at 105° C.) used to treat the organophosphate fluid. When the two essential regeneration process steps of leaching and heating are completed they may be repeated if desired to more completely regenerate the alumina. The adequacy of the regeneration treatment is determined by testing an aliquot portion of used organophosphate functional fluid with a selected amount of regenerated activated alumina to observe if acidity is reduced to the extent desired.

The leachate obtained from contact with the used activated alumina contains organophosphate functional fluid (originally entrained or sorbed by the alumina) as well as acid-causing substances. The organophosphate and polar organic solvent components of the leachate are easily recovered by distillative techniques. Typically, the leachate is distilled to yield a first distillate of relatively low boiling polar organic solvent. Next, the organophosphate is recovered as distillate at higher distillation temperatures and reduced pressure. The relatively high boiling residue (presumably derived from acid-causing materials) is discarded as waste. The purified solvent may be recycled to the regeneration step of the process. Purified organophosphate may be reformulated to prepare replacement organophosphate functional fluid.

DESCRIPTION OF THE DRAWING

The drawing is a flow diagram illustrating one embodiment of the process of the invention.

A used acidic organophosphate functional fluid enters via line 1, and activated alumina enters via line 3 to fluid contact chamber 5. The acidic fluid and alumina are contacted for a period of time sufficient to reduce acidity to an acceptable level and the resultant reclaimed organophosphate functional fluid is withdrawn from chamber 5, via line 7 for reuse. The used activated alumina exits chamber 5, via line 9 and enters leach zone 11 where it is leached with polar organic solvent entering via line 13. Leached activated alumina exits via line 15 to heating and vaporization zone 17 where polar organic solvent is withdrawn, via line 18 and recirculated to the process leach zone, via line 13. A substantially solvent-free regenerated active alumina exits from zone 17, via line 19 to be transferred, via line 3 to contact chamber 5 for reuse.

The polar organic solvent leachate exits zone 11, via line 21 to distillation, column 23. Purified polar organic solvent is removed as overhead from distillation column 23, via line 25 for recirculation to solvent input line 13. Likewise, organophosphate distillate is removed from column 23, via line 27 for addition to organophosphate product output stream 7. A high boiling waste distilland exits the distillation zone, via line 29.

The following examples illustrate the practice of the invention:

EXAMPLE 1

This example illustrates repeated regeneration of activated alumina used for removing acidity from organophosphate functional fluid.

A 500 gram sample of used Fyrquel ® 150 functional fluid (t-butylphenyl/phenyl phosphate) having an acid number (ASTM D 974) of 0.30 mg. KOH/g was combined with 2 weight percent new activated alumina (F-1 grade, 24-48 mesh, product of Alcoa Corp.) and the mixture stirred at 54° C. to 65° C. for two hours. The mixture was then filtered and the filtrate found to have an acid number of 0.09 mg. KOH/g.

The solid activated alumina residue obtained from the operations described in the preceding paragraph was recovered and slurried at room temperature three times with separate 50 ml. portions of methyl alcohol. Thereafter, the alcohol and alumina were separated by filtration. Each alcohol wash was saved. The alcohol solvent leached alumina was dried at 149° C. in an oven for thirty minutes. A dried regenerated alumina weighing 112% of the original weight of alumina was recovered.

A second 500 gram sample of used Fyrquel ® 150 functional fluid of acid number 0.3 mg. KOH/g was slurried for two hours with two weight percent of the previously regenerated alumina at a temperature of 54° C. to 65° C. for two hours. Thereafter, the mixture was filtered and the filtrate found to have an acid number of 0.09 mg. KOH/g.

Recovery and reuse of the alumina was again performed using the method described in the preceding paragraphs. The alcohol leached alumina was dried in a 149° C. oven for 30 minutes and the reclaimed alumina obtained in 100% by weight yield.

The twice reclaimed alumina was again mixed with 500 grams of used Fyrquel ® 150 functional fluid (acid number 0.30 mg. KOH/g) at a treatment level of 2 weight percent. The mixture was slurried at 54° C. to 65° C. for two hours, filtered and the filtrate found to have an acid number of 0.19 mg. KOH/g.

EXAMPLE 2

This example illustrates the reduction of acidity in phosphate ester functional fluids followed by regeneration of the acid-removal agent.

A 410 gram sample of used Fyrquel ® GT functional fluid (t-butylphenyl/phenyl phosphate) having an acid number of 0.65 mg. KOH/g. was stirred with 30 grams of activated alumina, F-1 grade, (product of Alcoa Co.) at 60°-65° C. for a period of two hours. At the conclusion of the two hour period the fluid was found to have an acid number of 0.10 mg. KOH/g. The solid alumina residue was washed three times with separate 100 ml. volumes of acetone. 29.5 grams of the acetone leached alumina was heated in an oven at 600° C. for a period of one hour. The resultant leached and heated alumina was saved for reuse in reducing acidity of additional samples of Fyrquel ® GT.

A part of the alumina regenerated by the method of the preceding paragraph was contacted at a 2 weight percent treatment level with a sample of used Fyrquel ® GT functional fluid having an acid number of 0.65 mg. KOH/g. The mixture was stirred at 60° C. for two hours and filtered. After treatment with the alumina the Fyrquel ® fluid had an acid number of 0.28 mg. KOH/g.

A second part of the alumina represented by the method of this example was contacted at a 6 weight percent treatment level with a sample of used Fyrquel ® GT functional fluid having an acid number of 0.65 mg. KOH/g and the mixture stirred at 60° C. for one hour. After treatment with the alumina the filtered Fyrquel ® fluid had an acid number of 0.06 mg. KOH/g.

EXAMPLE 3

This example illustrates the acid and corrosion reducing action of activated alumina for the treatment of organophosphate functional fluids.

A 500 gram sample of Fyrquel ® GT (t-butylphenyl/phenylphosphate) functional fluid having an acid number of 0.63 mg. KOH/gram was contacted with eight weight percent of activated alumina (F-1 grade, product of Alcoa Corp.), and the mixture was stirred for two hours at 55° C.

The treated fluid was separated from the alumina by filtration and evaluated in an oxidative stability test conducted at 175° C. for 72 hours (Federal Test Method Procedure 791 B Method 5308.6). The oxidative stability test subjected the fluid to an air flow of five liters per hour in the presence of various metals. Used Fyrquel ® GT fluid and new Fyrquel ® GT fluid were evaluated for comparison in the same oxidation test. The test results are summarized in the table as follows:

TABLE

| Fryquel ® GT treatment | % change In Viscosity | Change in Acid number mg. KOH/gram | Metal weight loss, mg/Cm$_2$. | | | | |
|---|---|---|---|---|---|---|---|
| | | | Mg | Steel | Al | Ag | Cu |
| Used Fluid (no alumina treatment) | 1.14 | .43 | .004 | .008 | nil | .0004 | .785 |
| Used Fluid Alumina treated | 2.05 | .02 | .004 | .004 | .012 | nil | .004 |
| New Fluid | .59 | .01 | nil | .007 | nil | .057 | nil |

I claim:
1. A method of reducing the acidity of used organophosphate functional fluids by contact with activated alumina, directly returning said activated alumina contacted fluid for reuse, and subsequently regenerating the acid-reducing alumina which comprises the sequential steps of:
   (A) contacting said used organophosphate with an acid reducing amount of acid reducing agent consisting essentially of activated alumina,
   (B) separating the alumina of step (A) from the organophosphate
   (C) leaching the alumina of step (B) with a polar organic solvent,
   (D) separating the alumina of step (C) from the leachate and thereafter heating the alumina at a temperature of less than 160° C.

2. The method of claim 1 wherein the organophosphate is selected from the group consisting of isopropylphenyl/phenyl phosphate, secondarybutylphenyl/phenyl phosphate, and tertiarybutylphenyl/phenyl phosphate.

3. The method of claim 1 wherein the organophosphate is contacted with at least about one to about five percent of activated alumina based on the weight of organophosphate.

4. The method of claim 1 wherein the polar organic solvent is selected from the group consisting of ketones, alcohols, and mixtures thereof having less than seven carbon atoms.

5. The method of claim 4 wherein the polar organic solvent is selected from the group consisting of methanol, ethanol, propanol, isopropanol, butanol, acetone, methyl ethyl ketone, and mixtures thereof.

6. The method of claim 5 wherein the polar organic solvent is selected from methanol, ethanol, and acetone.

7. The method of claim 1 or 2 or 6 wherein the alumina contact time of step (A) is from about one-half hour to about twelve hours.

8. The method of claim 1 or 2 or 6 wherein the alumina resulting from step (D) is recycled to step (A).

* * * * *